(12) United States Patent
Sasaki et al.

(10) Patent No.: US 10,098,682 B2
(45) Date of Patent: Oct. 16, 2018

(54) HIGH PRESSURE REMOTE DELIVERY SYSTEM FOR CEMENT AND METHODS OF USE

(71) Applicant: Kyphon SÀRL, Neuchatel (CH)

(72) Inventors: Neil S. Sasaki, San Jose, CA (US); Michael A. Smith, San Jose, CA (US)

(73) Assignee: Medtronic Holding Company Sárl, Tolochenaz (CH)

( * ) Notice: Subject to any disclaimer, the term of this patent is extended or adjusted under 35 U.S.C. 154(b) by 663 days.

(21) Appl. No.: 14/305,850

(22) Filed: Jun. 16, 2014

(65) Prior Publication Data

US 2015/0359579 A1    Dec. 17, 2015

(51) Int. Cl.
*A61B 17/60*    (2006.01)
*A61B 17/88*    (2006.01)

(52) U.S. Cl.
CPC ................ *A61B 17/8822* (2013.01)

(58) Field of Classification Search
CPC .................................. A61B 17/8822
USPC .............. 606/92–94; 604/181, 187, 533–539
See application file for complete search history.

(56) References Cited

U.S. PATENT DOCUMENTS

| | | | |
|---|---|---|---|
| 3,741,247 A | 6/1973 | Kaemmer | |
| 4,485,014 A * | 11/1984 | Gilroy | A61M 5/165 210/321.84 |
| 4,668,217 A * | 5/1987 | Isono | A61M 39/10 604/29 |
| 5,176,415 A * | 1/1993 | Choksi | A61M 39/10 128/202.27 |
| 6,210,359 B1 | 4/2001 | Patel et al. | |
| 6,705,082 B2 | 3/2004 | Ju | |
| 7,686,596 B2 | 3/2010 | Clausen et al. | |
| 8,415,407 B2 | 4/2013 | Beyar et al. | |
| 8,500,717 B2 * | 8/2013 | Becker | A61M 39/10 604/534 |
| 2003/0078589 A1 * | 4/2003 | Preissman | A61B 17/8819 606/93 |

(Continued)

FOREIGN PATENT DOCUMENTS

| | | |
|---|---|---|
| CN | 203576627 U | 5/2014 |
| WO | 2010051386 A1 | 5/2010 |

OTHER PUBLICATIONS

International Search Report and Written Opinion for PCT/US2015/035488 the counterpart application dated Aug. 28, 2015, 24 pages.

*Primary Examiner* — Matthew Lawson

(57) ABSTRACT

A high pressure bone cement delivery device includes a delivery adapter having an input port, an output port and cavity having bone cement disposed therein. A pressure intensifier is coupled to the delivery adapter and includes a first chamber containing a gas, a second chamber containing a fluid. The pressure intensifier includes a piston having a first end movably disposed within the first chamber and a second end movably disposed in the second chamber. The pressure intensifier includes a second output port in communication with the second chamber and the input port. The first end of the piston includes a first end surface having a first surface area and the second end of the piston comprises a second end surface having a second surface area that is less than the first surface area. Methods of use are disclosed.

20 Claims, 6 Drawing Sheets

(56) References Cited

U.S. PATENT DOCUMENTS

| | | | |
|---|---|---|---|
| 2005/0070915 A1* | 3/2005 | Mazzuca | A61B 17/8822 606/93 |
| 2006/0074433 A1* | 4/2006 | McGill | A61B 17/8822 606/92 |
| 2011/0015641 A1 | 1/2011 | Matsumoto | |
| 2012/0191101 A1 | 7/2012 | Roth et al. | |
| 2012/0191102 A1* | 7/2012 | Matsumoto | A61B 17/8822 606/94 |

* cited by examiner

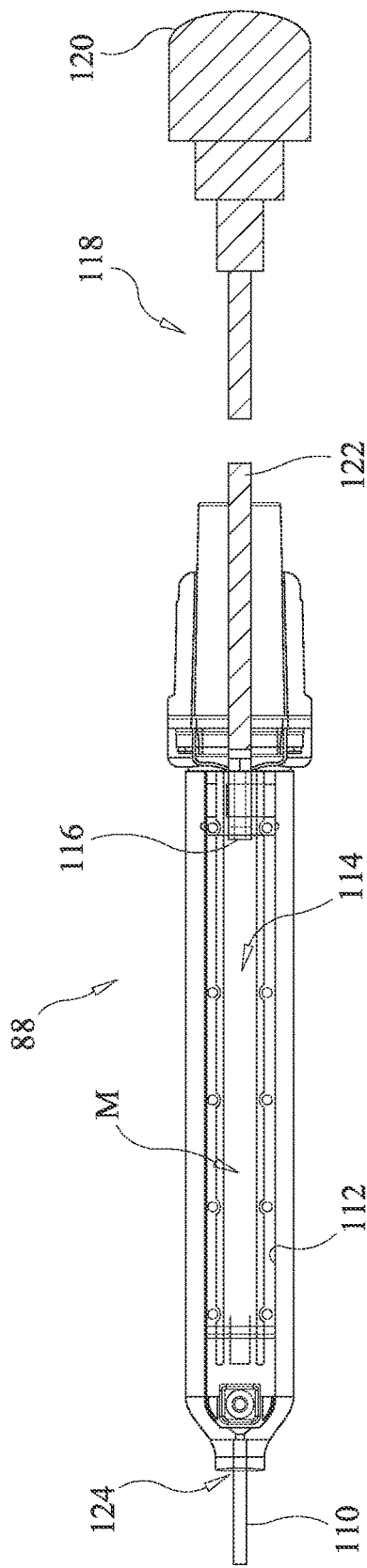
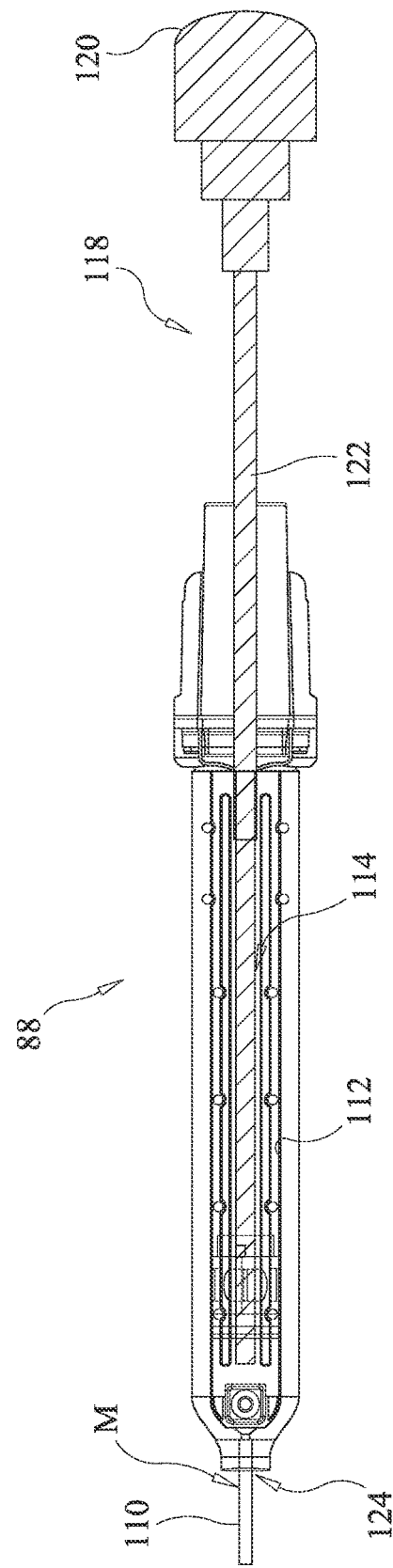
FIG. 4
FIG. 4A

US 10,098,682 B2

HIGH PRESSURE REMOTE DELIVERY SYSTEM FOR CEMENT AND METHODS OF USE

TECHNICAL FIELD

The present disclosure generally relates to medical devices for bone repair, and more particularly to a medical system and method for mixing and dispensing bone cement or other materials.

BACKGROUND

Many medical procedures employ medical grade cement in connection with the restoration and strengthening of bone structures. During such procedures, cement is typically dispensed to a bone to fill in voids or spaces in the bone or between medical devices or implants attached to or embedded within the bone. These dispensing devices may include systems as simple as syringes and as complex as electronically controlled valves.

Due to the medical nature of some procedures, the amount and placement of the fluids, such as, cement, in some situations may need to be administered under pressure. For example, some bone cements are highly viscous and require significant pressure to expel the bone cement from a dispensing system, such as, for example, a syringe. Despite the simplicity or complexity of the dispensing system, control over when, where, how much and at what pressure cement is dispensed is of concern. Currently, there is a need for a high pressure delivery system for cement that is easy to manufacture, easy to use, produces acceptable pressurized delivery of cement and would permit for fewer steps or less complicated steps in a high pressure dispensing process. This disclosure describes improvements over these prior art technologies in providing improved systems for dispensing bone cement.

SUMMARY

Accordingly, a high pressure bone cement delivery device is provided that comprises a delivery adapter comprising an input port, an output port and cavity having bone cement disposed therein. The high pressure bone cement delivery device also comprises a pressure intensifier coupled to the delivery adapter. The pressure intensifier comprises a first chamber containing a gas, a second chamber containing a fluid, a piston having a first end movably disposed within the first chamber and a second end movably disposed in the second chamber, and a second output port in communication with the second chamber and the input port. The first end of the piston comprises a first end surface having a first surface area and the second end of the piston comprises a second end surface having a second surface area that is less than the first surface area.

In one embodiment, in accordance with the principles of the present disclosure, the high pressure bone cement delivery device comprises a delivery adapter comprising an input port, an output port and cavity having bone cement disposed therein. The high pressure bone cement delivery device further comprises a pressure intensifier connected to the delivery adapter by a hollow tube. The pressure intensifier comprises a first chamber containing a gas, a second chamber containing a hydraulic fluid, a piston having a first end movably disposed within the first chamber and a second end movably disposed in the second chamber. The first and second ends of the piston each comprises a groove having an O-ring disposed therein. The O-rings engage an inner surface of the pressure intensifier that defines the first and second chambers to create a water tight seal. A second output port of the pressure intensifier is in communication with the second chamber and the input port. A pressurized syringe is connected to the pressure intensifier by a hollow tube. The pressurized syringe comprises a plunger. The first end of the piston comprises a first end surface having a first surface area and the second end of the piston comprises a second end surface having a second surface area that is less than the first surface area. The first chamber has a diameter that is greater than that of the second chamber. The gas has a first pressure when the gas is disposed in the first chamber. Axial translation of the plunger in a first direction moves the piston in a first direction such that the gas is vented through a vent in the pressure intensifier and the hydraulic fluid moves through the second output port and into the input port such that the hydraulic fluid acts on a piston that moves the bone cement out of the output port at a second pressure that is greater than the first pressure.

In one embodiment, in accordance with the principles of the present disclosure, a method of delivering high pressure bone cement comprises providing a high pressure bone cement delivery device that comprises a delivery adapter comprising an input port, an output port and cavity having bone cement disposed therein. The high pressure bone cement delivery device also comprises a pressure intensifier coupled to the delivery adapter. The pressure intensifier comprises a first chamber containing a gas, a second chamber containing a fluid, a piston having a first end movably disposed within the first chamber and a second end movably disposed in the second chamber, and a second output port in communication with the second chamber and the input port. The first end of the piston comprises a first end surface having a first surface area and the second end of the piston comprises a second end surface having a second surface area that is less than the first surface area. The output port is positioned to deliver the bone cement adjacent a surgical site. The piston is translated axially in a first direction such that the gas is vented through a vent in the pressure intensifier and the fluid moves through the second output port and into the input port such that the fluid acts moves the bone cement out of the output port and into the surgical site at a second pressure that is greater than a first pressure of the gas when the gas is disposed in the first chamber.

BRIEF DESCRIPTION OF THE DRAWINGS

The present disclosure will become more readily apparent from the specific description accompanied by the following drawings, in which:

FIG. 4 is a side, cross sectional view, in part phantom, of components of the system shown in FIG. 1;

FIG. 4A is a side, cross sectional view, in part phantom, of components of the system shown in FIG. 1.

Like reference numerals indicate similar parts throughout the figures.

DETAILED DESCRIPTION

Figure 1:
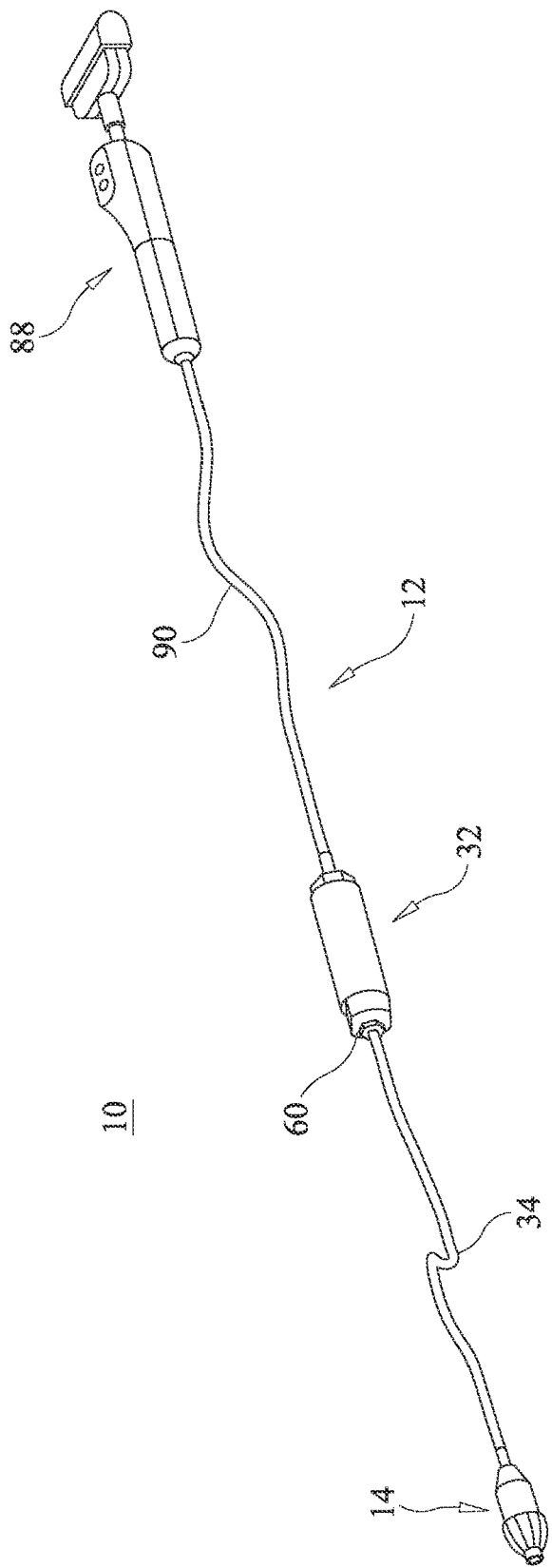
FIG. 1 is a perspective view of one embodiment of a bone cement delivery system in accordance with the principles of the present disclosure.

The exemplary embodiments of a bone cement delivery system and related methods are discussed in terms of medical devices for the treatment of skeletal injuries, disorders and repairs and more particularly, in terms of a high pressure bone cement delivery device and method for bone repair. It is envisioned that the system and method may be employed in applications such as correction of cracks, fissures, voids, e.g., due to osteoporosis or other diseases or injuries. In addition, the system and method may be employed with the placement of support structures or devices attached to or embedded within bone. For example, such structures may include pins, screws, replacement joints (e.g., of the hip, knee, shoulder), etc.

In some embodiments, the bone cement delivery system includes a pressure intensifier that is coupled to a bone cement delivery cartridge and a syringe, such as, for example, a pressurized syringe. In some embodiments, the bone cement delivery system is less expensive than conventional bone cement delivery systems. In some embodiments, the bone cement delivery system is less expensive to assemble than conventional bone cement delivery systems. In some embodiments, the bone cement delivery system has less small, moving parts than conventional bone cement delivery systems. In some embodiments, the bone cement delivery system includes a pressurized syringe that is adapted for use with conventional bone cement delivery systems.

It is contemplated that one or all of the components of the bone cement delivery system may be disposable, peel-pack, pre-packed sterile devices. One or all of the components of the bone cement delivery system may be reusable. The high pressure bone cement delivery device may be configured as a kit with multiple sized and configured components.

It is envisioned that the present disclosure may be employed to treat or repair bone injuries or disorders such as, for example, osteoporosis, joint replacement, fracture repairs, bone breaks, etc. It is contemplated that the present disclosure may be employed with other osteal and bone related applications, including those associated with diagnostics and therapeutics, such as the delivery of a therapeutic agents to a site for treatment or the delivery of radio opaque markers for tracking fluid once it is released into a patient. It is further contemplated that the disclosed bone cement delivery system and methods may be alternatively employed in a surgical treatment with a patient in a prone or supine position, and/or employs various surgical approaches, including anterior, posterior, posterior mid-line, direct lateral, postero-lateral, antero-lateral approaches, etc. in any body region. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a mixer gun system and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-5, there are illustrated components of a bone cement delivery system 10 including a high pressure bone cement delivery device 12 in accordance with the principles of the present disclosure.

The components of system 10 can be fabricated from biologically acceptable materials suitable for medical applications, including metals, synthetic polymers, ceramics and bone material and/or their composites, depending on the particular application and/or preference of a medical practitioner. For example, the components of system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 is employed, for example, with an open, mini-open or minimally invasive surgical technique to fill voids, provide patches, attach prosthetic devices, etc., or any other bone related repairs.

Device 12 includes a delivery adapter 14 comprising an inner surface 16 defining a cavity 18 configured for disposal of a filler material, such as, for example, bone cement BC. Adapter 14 extends from an end 20 to an opposite end 22. End 20 includes an output port 24 having an opening 26 that is in communication with cavity 18. End 22 includes an input port 28 having an opening 30 that is in communication with cavity 18. In some embodiments, end 20 defines a portion 20a of adapter 14 and end 22 defines a portion 22a of adapter. Portion 20a comprises an inner thread form 21 that engages an external thread form 23 of portion 22a to removably connect portion 20a with portion 22a. Adapter 14 is configured such that pressure entering cavity 18 through opening 30 will move bone cement BC in the direction shown by arrow A until bone cement BC exits adapter 14 through opening 26. In some embodiments, portion 20a comprises an inner surface 25 defining a nozzle 27 having a section 27a that is in communication with cavity 18 and a section 27b that is in communication with section 27a and opening 26. Section 27b has a diameter that is less than that of section 27a. Nozzle 27 comprises a tapered section 27c that connects section 27a with section 27b.

In some embodiments, an outer surface 37 of portion 20a engages surface 18 such that the outer surface of portion 20a and surface 18 form a seal that is air tight or water tight. In some embodiments, the outer surface of portion 20a includes a groove 37a having an O-ring 17b disposed therein that engages surface 16 such that O-ring 37b forms a seal with surface 16 that is air tight or water tight. In some embodiments, adapter 14 comprises a piston, such as, for example, an actuator 29 movably disposed in cavity 18. In some embodiments, an outer surface of actuator 29 engages surface 16 to form a seal that is air tight or water tight. In some embodiments, the outer surface of actuator 29 includes an annular or circumferential groove 31 having an O-ring 33 disposed therein such that O-ring 33 form a seal that is air tight or water tight. In some embodiments, actuator 29 comprises a recess 29a on a side 29b of actuator 29 configured to at least provisionally receive bone cement BC to move actuator 29 in the direction shown by arrow A relative to cavity 18. In some embodiments, a side 29c of actuator 29 opposite side 29b is convexly curved and/or section 27a includes a beveled opening 27d that engages the convex portion of side 29c that forms a seal that is air tight or water tight.

Figure 5:
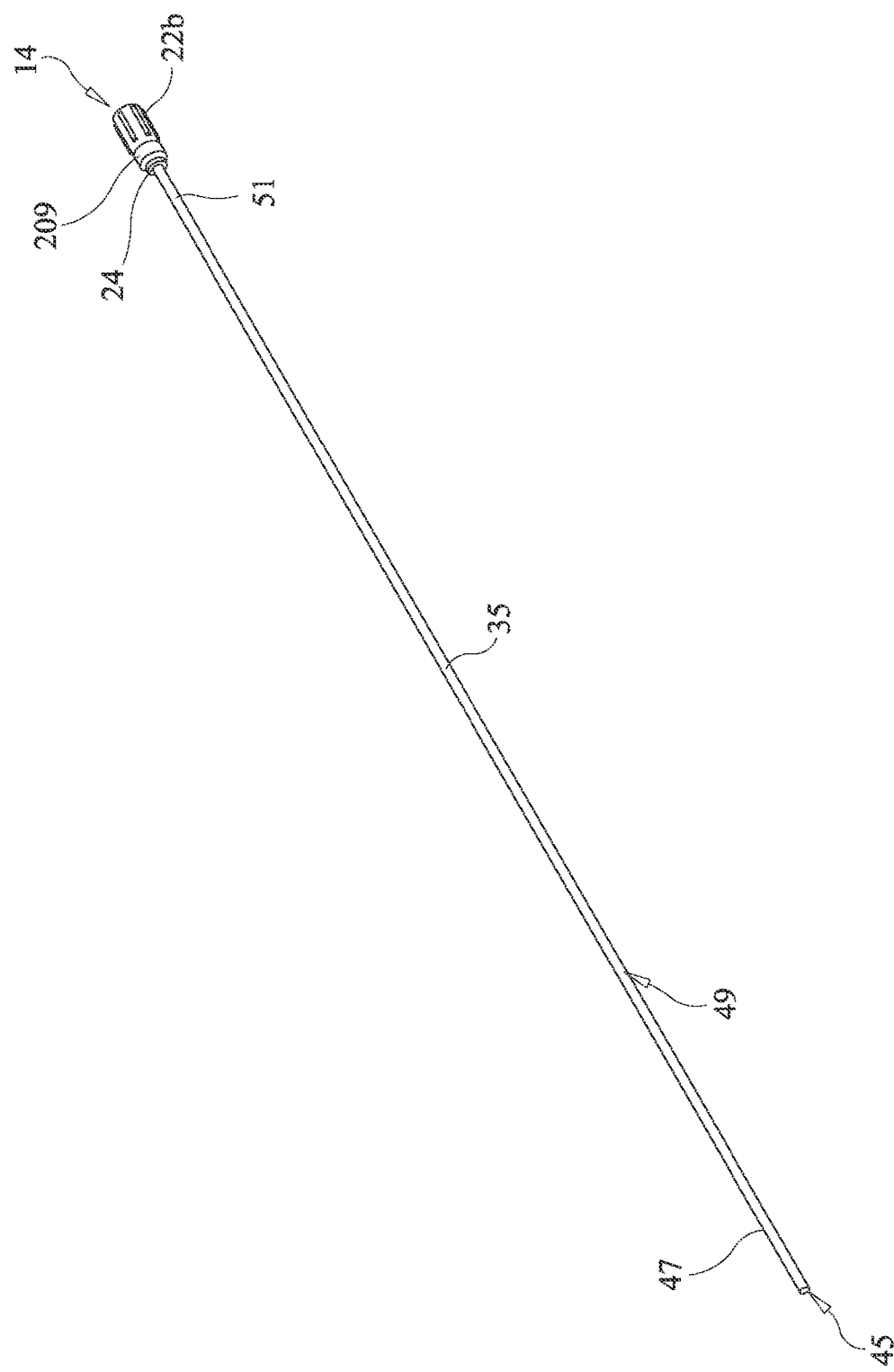
FIG. 5 is a perspective view of a component of the system shown in FIG. 1 connected with another component of the system, in accordance with the principles of the present disclosure.

In some embodiments, opening 26 and/or opening 30 may have various cross section configurations, such as, for example, oval, oblong, triangular, rectangular, square, polygonal, irregular, uniform, non-uniform, variable, tubular and/or tapered. In some embodiments, opening 30 may be disposed at alternate orientations, relative to opening 26, such as, for example, transverse, perpendicular and/or other angular orientations such as acute or obtuse, co-axial and/or may be offset or staggered. In some embodiments, portion 20a can be variously connected with portion 20b, such as, for example, monolithic, integral connection, frictional engagement, threaded engagement, mutual grooves, screws, adhesive, nails, barbs and/or raised element. In some embodiments, O-ring 33 and/or O-ring 37b comprises a flexible and/or compressible material, such as, for example, rubber or silicone that maintains a water tight and/or air tight seal with surface 16 as actuator 29 and/or portion 20a translates in the direction shown by arrow A and/or the direction shown by arrow B. In some embodiments, groove 31 and/or groove 37a has an arcuate and/or concave configuration to receive an arcuate and/or convex outer surface of O-ring 33 and/or O-ring 37a. In one embodiment, port 24 comprises an internal thread form 24a that engages a thread form on an outer surface of an extension tube 35, as shown in FIG. 5, for example. In some embodiments, tube 35 can be variously connected with adapter 14, such as, for example, monolithic, integral connection, frictional engagement, threaded engagement, mutual grooves, screws, adhesive, nails, barbs and/or raised element.

In some embodiments, cavity 18 is filled entirely with bone cement BC. In some embodiments, cavity 18 is only partially filled with bone cement BC. In some embodiments, bone cement BC comprises a poly(methyl methacrylate) (PMMA); methyl methacrylate (MMA); calcium phosphate; a resorbable polymer, such as, for example, PLA, PGA or combinations thereof; a resorbable polymer with allograft, such as, for example, particles or fibers of mineralized bone; Plexur® sold by Osteotech, Inc., and combinations thereof. In some embodiments, bone cement BC is a high viscosity bone cement. In some embodiments, bone cement BC has a viscosity that is at least 500 Pascal-sec (Pa-s) to infiltrate a medical site and prevent any migration of bone cement BC during medical procedures. In some embodiments, bone cement BC has a viscosity that is at least 600 Pa-s. In some embodiments, bone cement BC has a viscosity that is at least 800 Pa-s. In some embodiments, bone cement BC has a viscosity that is at least 1,000 Pa-s. In some embodiments, bone cement BC comprises a liquid component and a powder component. In some embodiments, the liquid component and the powder component are mixed or otherwise combined before bone cement BC is loaded into cavity 18. In some embodiments, portion 20*a* is rotated relative to portion 22*b* such that thread form 23 disengages thread form 21 and portion 20*a* is no longer connected to portion 22*b*. Bone cement BC is then loaded into cavity 18 via a cement mixer or syringe. In some embodiments, bone cement BC is loaded into cavity 18 by injecting bone cement BC through opening 26, through section 27*b*, through section 27*a* and into cavity 18. In some embodiments, the liquid component and the powder component are loaded into cavity 18 separately and mixed or otherwise combined within cavity 18. In some embodiments, the two components of bone cement BC are mixed within cavity 18 using pressure, mechanical agitation, static mixing, or combinations thereof. In some embodiments, the liquid component and the powder component are mixed or otherwise combined such that bone cement BC has a viscosity of at least 500 Pa-s. In some embodiments, the liquid component and the powder component mixed or otherwise combined such that bone cement BC has a viscosity of at least 500 Pa-s at 2 minutes after the initiation of mixing the two components. In some embodiments, the liquid component and the powder component mixed or otherwise combined such that bone cement BC has a viscosity of at least 500 Pa-s at 5 minutes after the initiation of mixing the two components. In some embodiments, the liquid component and the powder component mixed or otherwise combined such that bone cement BC has a viscosity of at least 500 Pa-s after 10 minutes or more from the initiation of mixing the two components. In some embodiments, bone cement BC comprises a polymerization accelerator. In some embodiments, bone cement BC has a viscosity such that a pressure between about 800 psi and about 1,500 psi is required to move bone cement BC in the direction shown by arrow A until bone cement BC exits adapter 14 through opening 26. In some embodiments, bone cement BC has a viscosity such that a pressure of at least 800 psi is required to move bone cement BC in the direction shown by arrow A until bone cement BC exits adapter 14 through opening 26. In some embodiments, bone cement BC has a viscosity such that a pressure of at least 1,000 psi is required to move bone cement BC in the direction shown by arrow A until bone cement BC exits adapter 14 through opening 26. In some embodiments, bone cement BC has a viscosity such that a pressure of at least 1,500 psi is required to move bone cement BC in the direction shown by arrow A until bone cement BC exits adapter 14 through opening 26.

Device 12 comprises a pressure intensifier 32 that is connected to adapter 14 by a tube, such as, for example, a hollow tube 34 having an inner surface defining a lumen 36. An end 38 of tube 34 is coupled to port 28 such that lumen 36 is in communication with opening 30. In some embodiments, tube 34 is flexible such that tube 34 can bend without breaking to facilitate navigating adapter 14 to a surgical site, such as, for example, a fractured bone, such as, for example, a fractured vertebra. In some embodiments, tube 34 is transparent or translucent to facilitate viewing of material within lumen 36. In some embodiments, lumen 36 has a uniform diameter along the entire length of tube 34. In some embodiments, tube 34 is rigid such that tube 34 cannot bend without breaking to provide strength to tube 34. In some embodiments, tube 34 is coupled to adapter 14 such that an outer surface of tube 34 engages surface 16. In some embodiments, tube 34 is coupled to adapter 14 such that the inner surface of tube 34 engages an outer surface of port 28. In some embodiments, tube 34 is coupled to adapter 14 by a bayonet connection system, a snap-fit connection system, etc. In some embodiments, end 38 comprises a connector 39 comprising an outer surface including an external thread form 39*a* that engages an internal thread form 41 of opening 30 to connect tube 34 with adapter 14. In some embodiments, tube 34 can be variously connected with adapter 14, such as, for example, monolithic, integral connection, frictional engagement, threaded engagement, mutual grooves, screws, adhesive, nails, barbs and/or raised element.

Intensifier 32 comprises an inner surface defining a chamber 42. In some embodiments, chamber 42 has a gas G disposed therein, such as, for example air. In some embodiments, chamber 42 is a vacuum. The inner surface of intensifier 32 also defines a chamber 44 containing a fluid, such as, for example, a hydraulic fluid HF. In some embodiments, hydraulic fluid HF comprises water, mineral oil, contrast, saline, biostatic water or combinations thereof. In some embodiments, hydraulic fluid HF is biocompatible and/or non-toxic to prevent injury in the event of leakage. In some embodiments, hydraulic fluid HF is biodegradable to prevent injury in the event of leakage. In some embodiments, hydraulic fluid HF is sterile and biocompatible.

Chamber 42 has a maximum diameter that is greater than that of chamber 44. In some embodiments, chamber 42 has a minimum diameter that is greater than a maximum diameter of chamber 44. Surface 40 includes a portion 46 defining a transition between chambers 42, 44. In some embodiments, portion 46 is tapered, stepped and/or radiused. Intensifier 32 extends along a longitudinal axis L between an end 48 and an opposite end 50. End 48 comprises an opening 52 that is in communication with chamber 44 and end 50 comprises an opening 54 that is in communication with chamber 42. An end 56 of tube 34 opposite end 38 is coupled to end 48 such that lumen 36 is in communication with opening 52 and/or chamber 44. In some embodiments, opening 52 comprises an internal thread form 58 and end 56 is coupled to an output port, such as, for example, a connector 60 comprising an external thread form 62 that mates with thread form 58 to removably connect tube 34 and/or connector 60 with intensifier 32. Connector 60 comprises an inner surface 64 defining a pathway 66 and a pathway 68 that is in communication with pathway 66. Pathways 66, 68 each have a uniform diameter along the entire length thereof. Pathway 66 has a diameter that is less than that of pathway 68. Pathways 66, 68 are each in communication with lumen 36 and chamber 44. In some embodiments, chamber 42 is unvented. In some embodiments, intensifier 32 comprises a vent 43 extending through surface 40 and an outer surface of intensifier 32. In some embodiments, vent 43 extends through portion 46. In some embodiments, vent 43 extends through chamber 42. In some embodiments, vent 43 includes a one vent extending through portion 46 and another vent extending through chamber 42.

In some embodiments, the outer surface of tube 34 engages surface 64 to connect tube 34 with connector 60. In some embodiments, tube 34 can be variously connected with connector 60, such as, for example, monolithic, integral connection, frictional engagement, threaded engagement, mutual grooves, screws, adhesive, nails, barbs and/or raised element. In some embodiments, opening 52, opening 54, pathway 66 and/or pathway 68 may have various cross section configurations, such as, for example, oval, oblong, triangular, rectangular, square, polygonal, irregular, uniform, non-uniform, variable, tubular and/or tapered. In some embodiments, opening 52, opening 54, pathway 66 and/or pathway 68 may be disposed at alternate orientations, relative to axis L, such as, for example, transverse, perpendicular and/or other angular orientations such as acute or obtuse, co-axial and/or may be offset or staggered. In some embodiments, tube 34 and/or connector 60 can be variously connected with intensifier 32, such as, for example, monolithic, integral connection, frictional engagement, threaded engagement, mutual grooves, screws, adhesive, nails, barbs and/or raised element. In some embodiments, lumen 36 has a uniform diameter along the entire length of tube 34 and pathway 66 has a diameter that is substantially equivalent or equivalent to the diameter of lumen 36. In some embodiments, pathway 66 has a diameter that is greater than that of lumen 36. In some embodiments, lead 22 may have various cross section configurations, such as, for example, oval, oblong, triangular, rectangular, square, polygonal, irregular, uniform, non-uniform, variable, tubular and/or tapered. In some embodiments, vent 43 may be disposed at alternate orientations, relative to axis L, such as, for example, transverse, perpendicular and/or other angular orientations such as acute or obtuse, co-axial and/or may be offset or staggered. In some embodiments, vent 43 may have various cross section configurations, such as, for example, oval, oblong, triangular, rectangular, square, polygonal, irregular, uniform, non-uniform, variable, tubular and/or tapered.

A piston 70 is disposed within intensifier 32 such that piston 70 is movable along axis L in the direction shown by arrow A and/or the direction shown by arrow B. Piston 70 comprises an end 72 positioned in chamber 42 and an opposite end 74 positioned in chamber 44. Ends 72, 74 are connected by a shaft 75. In some embodiments, outer surfaces of ends 72, 74 engage surface 40 to create a seal that is water tight and/or air tight. In some embodiments, end 72 includes a circumferential and/or annular groove 76 having an O-ring 78 disposed therein that engages surface 40 to create a seal that is water tight and/or air tight. In some embodiments, end 74 includes a circumferential and/or annular groove 80 having an O-ring 82 disposed therein that engages surface 40 to create a seal that is water tight and/or air tight. In some embodiments, O-ring 78 and/or O-ring 82 comprise a flexible and/or compressible material, such as, for example, rubber or silicone that maintains a water tight and/or air tight seal with surface 40 as piston 70 translates along axis L in the direction shown by arrow A and/or the direction shown by arrow B. In some embodiments, groove 76 and/or groove 80 have an arcuate and/or concave configuration to receive an arcuate and/or convex outer surface of O-ring 78 and/or O-ring 82. In some embodiments, ends 72, 74 each have a cylindrical cross sectional configuration. End 72 comprises an end surface 84 and end 74 comprises an end surface 86 opposite surface 84. Surface 84 has a surface area that is greater than that of surface 86. In some embodiments, the surface area of surface 84 is between about 50% and about 200% greater than the surface area of surface 86. In some embodiments, the surface area of surface 84 is 50% greater than the surface area of surface 86. In some embodiments, the surface area of surface 84 is 75% greater than the surface area of surface 86. In some embodiments, the surface area of surface 84 is 100% greater than the surface area of surface 86. In some embodiments, the surface area of surface 84 is 150% greater than the surface area of surface 86. In some embodiments, the surface area of surface 84 is 200% greater than the surface area of surface 86.

Intensifier 32 is connected to a pump, such as, for example, a pressurized syringe 88 by a tube, such as, for example, a hollow tube 90. In some embodiments, an end 92 of tube 90 is coupled to an end cap 94 having an external thread form 96 that engages an internal thread form 98 of opening 54 to connect end cap 94 with intensifier 32. End cap 94 comprises an inner surface 100 defining a passageway 102 comprising a portion 104 and a portion 106. Portions 104, 106 each have a uniform diameter along the entire length thereof. In some embodiments, portion 104 has a diameter that is less than that of portion 106. Portion 106 is in communication with opening 54 and portion 104 is in communication with a lumen 108 defined by the inner surface of tube 90. In some embodiments, an outer surface of tube 90 engages surface 100 to couple tube 90 to end cap 94. In some embodiments, surface 40 defines a flange 105 extending perpendicular to axis L configured to engage an end surface 115 of end cap 94 to prevent end cap 94 from translating in the direction shown by arrow A passed flange 105. In some embodiments, tube 90 is flexible such that tube 90 can bend without breaking to facilitate navigating device to a surgical site, such as, for example, a fractured bone, such as, for example, a fractured vertebra. In some embodiments, lumen 108 has a uniform diameter along the entire length of tube 90 that is greater than the diameter of lumen 36. In some embodiments, lumen 108 has a diameter that is equal to that of lumen 36. In some embodiments, tube 90 is transparent or translucent to facilitate viewing of material within lumen 108. In some embodiments, tube 90 is rigid such that tube 90 cannot bend without breaking to provide strength to tube 90. In some embodiments, tube 90 is coupled to end cap 94 such that an outer surface of tube 34 engages surface 40. In some embodiments, tube 90 can be variously connected with end cap 94, such as, for example, monolithic, integral connection, frictional engagement, threaded engagement, mutual grooves, screws, adhesive, nails, barbs and/or raised element.

An end 110 of tube 90 opposite end 92 is coupled to syringe 88 such that an opening in end 110 is in communication with an opening 124 of syringe 88. In some embodiments, the outer surface of tube 90 engages an inner surface 112 of syringe 88 that defines opening 124 and a compartment 114 configured for disposal of a material M, such as, for example, a fluid or a gas. In some embodiments, the gas is air. In some embodiments, the fluid is water, saline, contrast or hydraulic fluid, such as, for example, hydraulic fluid HF. In some embodiments, syringe 88 comprises a port (not shown) having an opening that is in communication with compartment 114 such that material M can be injected into compartment 114 through the opening in the port. A head 116 of a plunger 118 is movably disposed in compartment 114 such that an outer surface of head 116 engages surface 112 to create a seal that is water tight and/or air tight. In some embodiments, head 116 includes an annular or circumferential groove having an O-ring disposed therein that creates a seal with surface 112 that is water tight or air tight. Syringe 88 comprises a handle 120 positioned outside of compartment 114 that is connected to head 116 by a shaft 122. In some embodiments, material M is loaded into compartment 114 by inserting end 92 into a source of material M with plunger 118 translated maximally in the direction shown by arrow A, as shown in FIG. 4, before connecting end 92 with intensifier 32. Plunger 118 is moved in the direction shown by arrow B, as shown in FIG. 4A, to create a vacuum in chamber 42 that draws material M into compartment 114. In some embodiments, end 92 is connected with intensifier 32 after material M is loaded into compartment 114.

In assembly, operation and use, system 10 is employed with a surgical procedure, such as, for a treatment of bone injuries, to provide bone repairs, to strengthen or rebuild bones, etc. It is contemplated that one or all of the components of system 10 can be delivered as a pre-assembled device or can be assembled in situ. System 10 may be completely or partially revised, removed or replaced.

System 10 and accessories thereof, described above, can be employed during a surgical procedure for dispensing bone cement. In use, a medical practitioner obtains access to a surgical site including a bone, such as, for example, a vertebra in need of repair, in any appropriate manner, such as through incision and retraction of tissues. It is envisioned that system 10 can be used in any existing surgical method or technique including open surgery, mini-open surgery, minimally invasive surgery and percutaneous surgical implantation, whereby the bone is accessed through a mini-incision, or sleeve that provides a protected passageway to the area.

An incision is made in the body of a patient and a cutting instrument creates a surgical pathway for insertion of components of system 10, such as, for example, tube 35. A preparation instrument can be employed to prepare tissue surfaces of the bone, as well as for aspiration and irrigation of a surgical region according to the requirements of a particular surgical application. In some embodiments, tube 35 is inserted into the surgical pathway such that an opening 45 in an end 47 of tube 35 is positioned adjacent hole(s), fracture(s), void(s), depression(s), etc. in the bone that the medical practitioner desires to fill, at least partly, with bone cement BC to maintain or improve the bone's structural integrity. In some embodiments, an inner surface of tube 35 defines a lumen 49 that is in communication with opening 45 and an opening in an end 51 of tube 35 opposite end 47. The opening in end 51 is in communication with section 27b.

In some embodiments, the void in the bone to be filled is created using an inflatable bone tamp by inserting a balloon of the inflatable bone tamp into bone, such as, for example, cancellous bone and expanding the balloon to create the void. In some embodiments, the void in the bone to be filled is created naturally and/or by injury to the patient. In some embodiments, the void in the bone is created during part of a surgical procedure. In some embodiments, adapter 14 is pre-loaded with bone cement BC prior to positioning opening 45 adjacent the bone and/or the void. In some embodiments, gas G is pre-loaded into chamber 42 and hydraulic fluid HF is pre-loaded into chamber 44 prior to positioning opening 45 adjacent the bone. In some embodiments, gas G has a first pressure when gas G is in chamber 42 and hydraulic fluid HF has a second pressure when hydraulic fluid HF is in chamber 44. In some embodiments, the first pressure is less than the second pressure. In some embodiments, the first pressure is between about 50 psi and about 500 psi and the second pressure is about 250 psi to about 1,500 psi. In some embodiments, material M is pre-loaded into compartment 114 prior to positioning opening 45 adjacent the bone. In some embodiments, material M has a third pressure when material M is in compartment 114. In some embodiments, the third pressure is less than the first pressure and the second pressure. In some embodiments, the third pressure is less than the second pressure.

Figure 2:
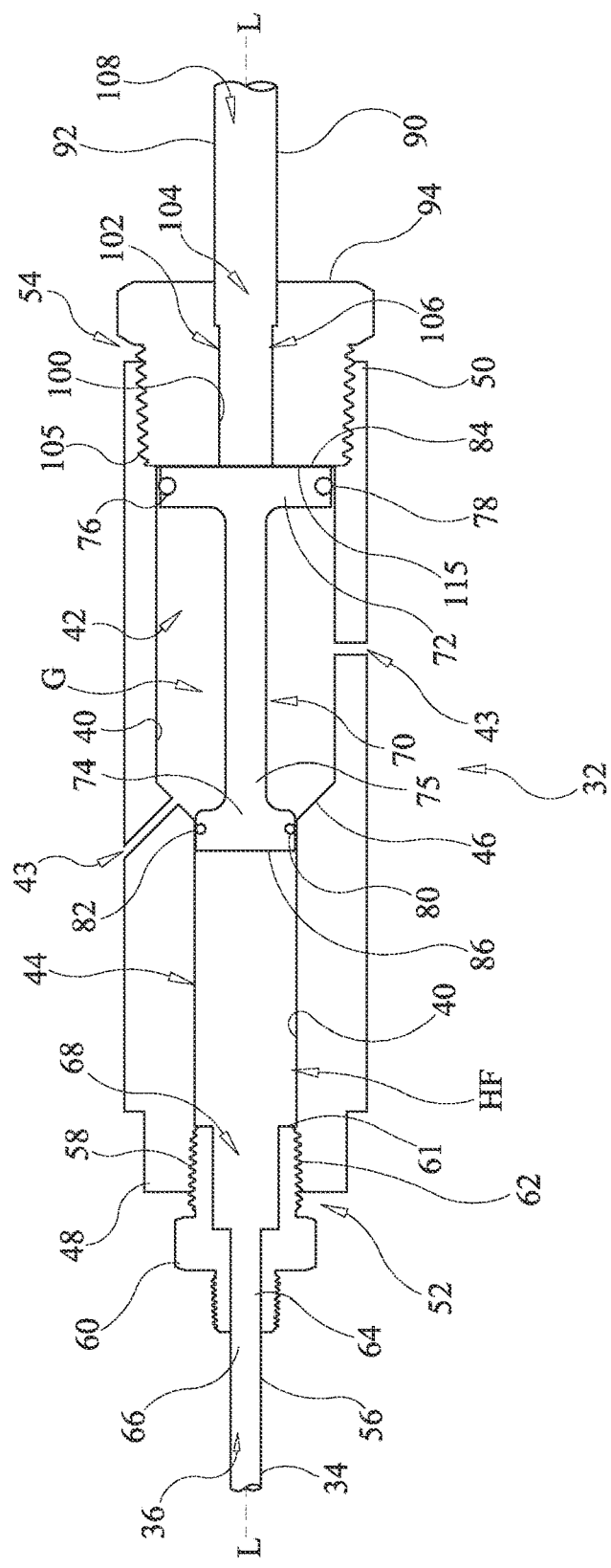
FIG. 2 is a side, cross sectional view of components of the system shown in FIG. 1.
Figure 2A:
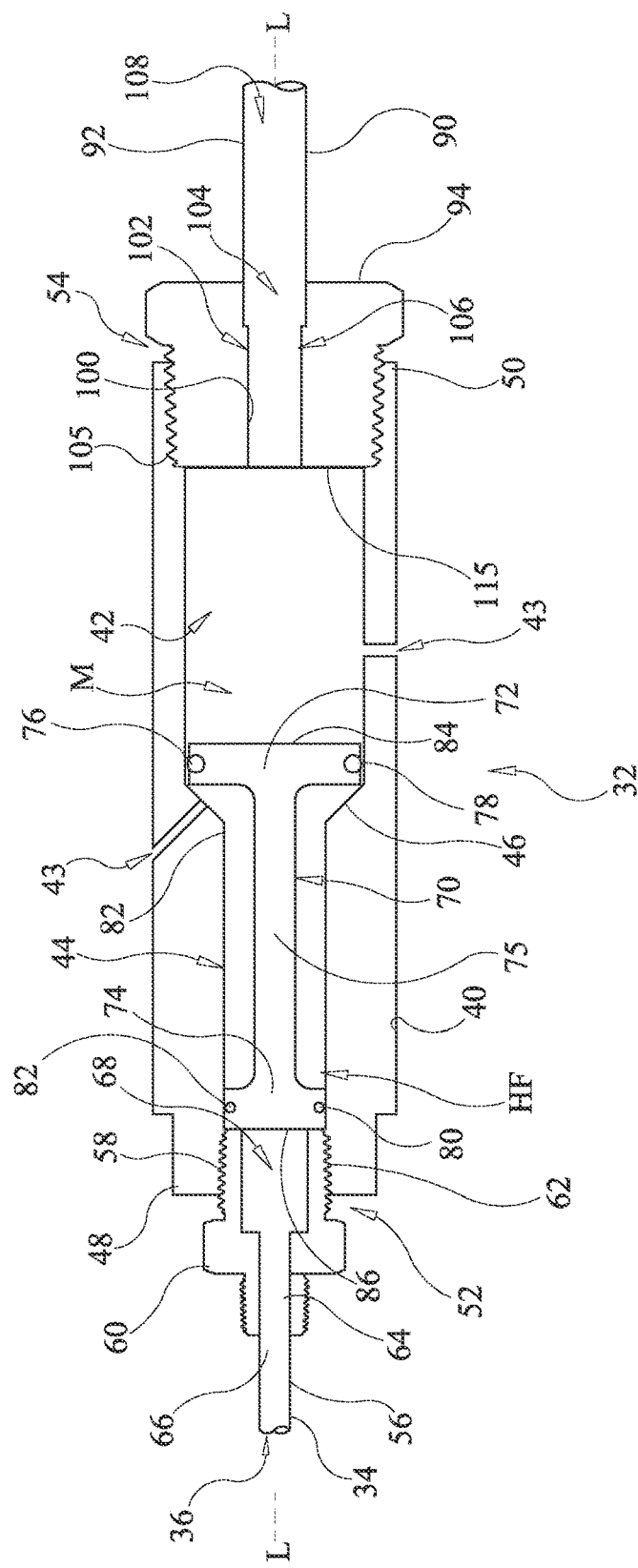
FIG. 2A is a side, cross sectional view of components of the system shown in FIG. 1.

The medical practitioner grips or otherwise engages handle 120 to move plunger 118 relative to compartment 114 in the direction shown by arrow A to move plunger 118 in the direction shown by arrow A between a first configuration in which head 116 is positioned a maximum distance from opening 124 within compartment 114, as shown in FIG. 4, to a second configuration in which head 116 is positioned adjacent opening 124, as shown in FIG. 4A. As plunger 118 moves from the first configuration to the second configuration, head 116 pushes material M in the direction shown by arrow A such that material M moves through out of opening 124, into the opening in end 110 and through lumen 108 toward intensifier 32. Material M moves out of the opening in end 92 and into portion 104. Material M moves out of portion 104 and into portion 106 such that material M applies a force and/or pressure upon surface 84. As material M applies a force and/or pressure upon surface 84, material M pushes piston 70 in the direction shown by arrow A to move piston 70 in the direction shown by arrow A between a first configuration in which surface 84 engages or is positioned adjacent surface 115, as shown in FIG. 2, and a second configuration in which surface 86 engages or is positioned adjacent an end surface 61 of connector, as shown in FIG. 2A.

As piston 70 moves between the first configuration of piston 70 and the second configuration of piston 70, at least some of gas G is vented through vent 43 and at least some of hydraulic fluid HF moves from chamber 44 and into pathway 68. In some embodiments, hydraulic fluid HF increases pressure as hydraulic fluid HF moves from chamber 44 and into pathway 68. Hydraulic fluid HF moves from pathway 68 and into pathway 66. In some embodiments, the pressure of hydraulic fluid HF increases as hydraulic fluid HF moves from pathway 68 and into pathway 66. Hydraulic fluid HF moves from pathway 66 and into an opening at end 56. Hydraulic fluid HF moves from end 56, through lumen 36 and out of an opening in end 38. Hydraulic fluid HF moves out of the opening in end 38, through opening 30 and into cavity 18.

Figure 3:
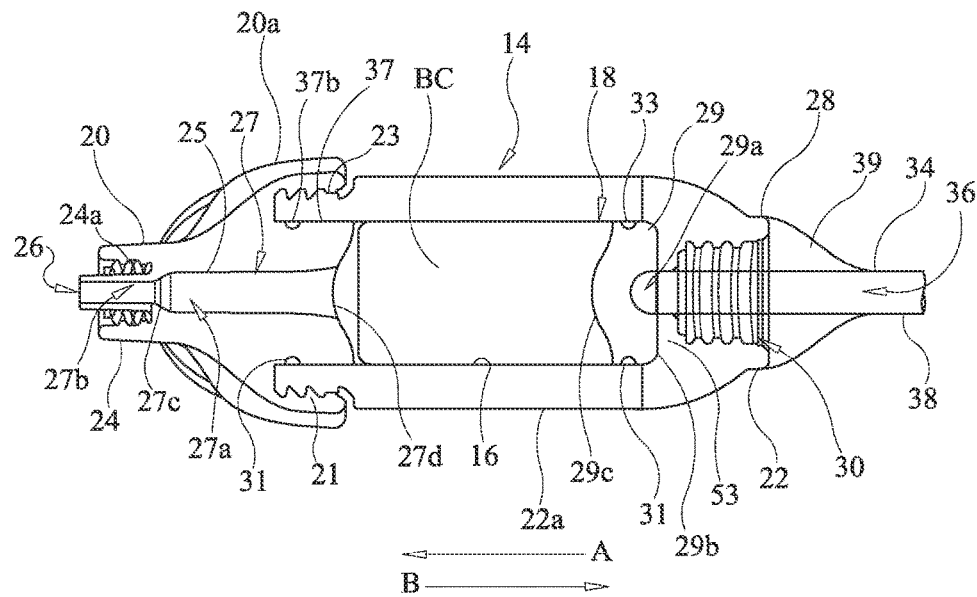
FIG. 3 is a side, cross sectional view of components of the system shown in FIG. 1.
Figure 3A:
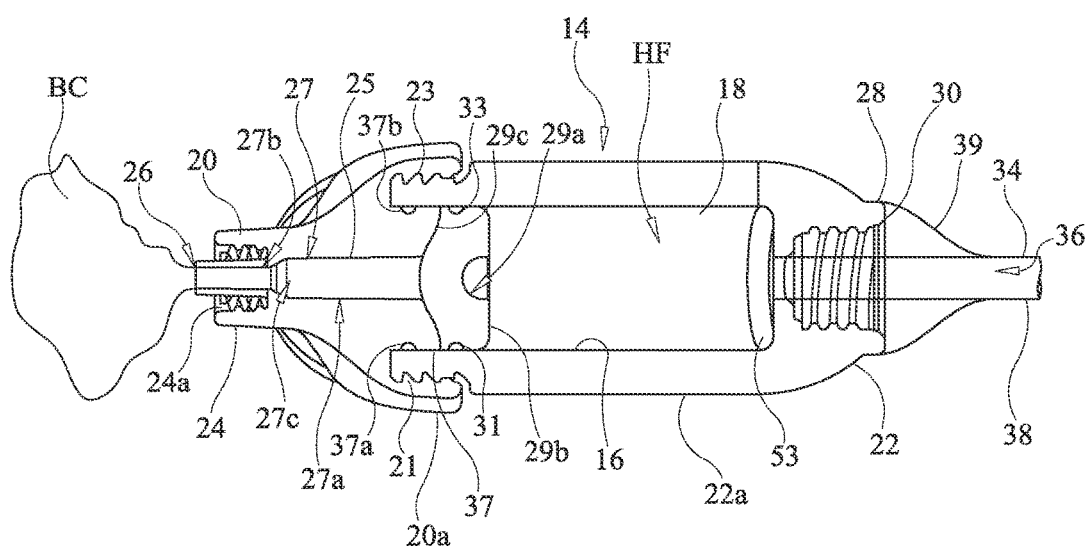
FIG. 3A is a side, cross sectional view of components of the system shown in FIG. 1.

In some embodiments, hydraulic fluid HF fills recess 29 and then fills the remaining portion of cavity 18 between side 29b and a transverse wall 53 such that hydraulic fluid applies a force and/or pressure upon actuator 29 to move actuator 29 in the direction shown by arrow A between a first configuration in which side 29b engages or is positioned adjacent wall 53 and bone cement BC is positioned between side 29c and portion 20a, as shown in FIG. 3, and a second configuration in which side 29c engages portion 20a and bone cement BC is expelled through opening 26, as shown in FIG. 3A. In some embodiments, bone cement BC is expelled through opening 26 and into the opening at end 51 such that bone cement BC moves through lumen 49 and out of tube 35 through opening 45 and into the fracture or void in the bone to at least partially fill the fracture or void. In some embodiments, bone cement BC is allowed to cure within the facture or void. In some embodiments, hydraulic fluid HF may be required to have a pressure of at least 800 psi in order to allow actuator 29 to push bone cement BC through cavity 18, out of opening 26, through lumen 49 and/or out of opening 45. In some embodiments, the pressure of at least 800 is required due to the viscosity of bone cement BC. In some embodiments, hydraulic fluid HF may be required to have a pressure of at least 1,500 psi in order to allow actuator 29 to allow actuator 29 to push bone cement BC through cavity 18, out of opening 26, through lumen 49 and/or out of opening 45. In some embodiments, the pressure of at least 1,500 is required due to the viscosity of bone cement BC. In some embodiments, hydraulic fluid HF may be required to have a pressure between about 800 psi and about 1,500 psi in order to allow actuator 29 to push bone cement BC through cavity 18, out of opening 26, through lumen 49 and/or out of opening 45.

In one embodiment, system 10 may also deliver an agent, which may be mixed in the bone cement BC or delivered separately. It is envisioned that the agent may include bone growth promoting material. In some embodiments, cavity 18 is pre-loaded with the agent before bone cement BC is loaded into cavity 18 and/or delivered to at least partially fill the bone. Device 12 then is used to expel the agent through opening 45 in the same manner as bone cement BC is expelled from opening 45, discussed above, such that the agent penetrates at least a portion of the bone fracture or void. Device 12 is then removed from the surgical site through the surgical pathway and bone cement BC is preloaded into cavity 18. Bone cement BC is then expelled from opening 45 by moving plunger 118 in the direction shown by arrow A, as discussed above. In some embodiments, device 12 is removed from the surgical pathway after the bone is at least partially filled with bone cement and the agent is loaded into cavity 18. Device 12 is then reinserted into the surgical pathway such that opening 45 is positioned adjacent the at least partially filled bone. Device 12 then is used to expel the agent through opening 45 in the same manner as bone cement BC is expelled from opening 45 by moving plunger 118 in the direction shown by arrow A, discussed above.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of correction system 10 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair bone deterioration or damage, with the aid of the system 10. Upon completion of the procedure, the surgical instruments and assemblies are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A high pressure bone cement delivery device comprising:
   a delivery adapter comprising a first input port adjacent a first end thereof, a first output port adjacent a second end thereof, an internal cavity portion, an actuator moveably disposed in the internal cavity portion, and a bone cement receiving area defined in part by the internal cavity portion and the actuator, the output port comprising a first section having a maximum diameter that is less than a maximum diameter of the internal cavity portion, a second section having a maximum diameter that is less than the maximum diameter of the first portion and a tapered section that connects the first section with the second section, the actuator being moveable between a first position adjacent to the first end and a second position adjacent the second end, the bone cement receiving area being larger with the actuator in the first position than with the actuator in the second position, movement of the actuator from the first position to the second position decreasing the size of the bone cement receiving area and forcing bone cement received therein to exit the internal cavity portion through the first output port, the delivery adapter having a first portion extending from the first end toward the second end, a second portion extending from the second end toward the first end, the first and second portions being removably attached to one another, the internal cavity portion being formed in the first portion, the first output port being formed in the second portion, and a portion of the second portion being received in the internal cavity portion;
   a pressure intensifier coupled to the delivery adapter and comprising:
      a body including a first chamber containing a gas and a second chamber containing a fluid,
      a piston having a first end portion movably disposed within the first chamber and a second end portion movably disposed in the second chamber, the first end portion of the piston comprising a first end surface having a first surface area, and the second end portion of the piston comprising a second end surface having a second surface area, the first surface area being greater than the second surface area, and
      a second output port in communication with the second chamber and the first input port, the second output port comprising a connector that is removably coupled to the body, the connector having a first end that includes a first pathway and a second end that includes a second pathway, the first pathway having a diameter that is less than a minimum diameter of the second chamber, the second pathway having a diameter that is less than the diameter of the first pathway; and
   a tube having a first end that is coupled to the second end of the connector and a second end that is coupled to the first input port.

2. A high pressure bone cement delivery device as recited in claim 1, wherein:
   the bone cement has a first pressure when the bone cement is disposed in the internal cavity; and
   axial translation of the piston in a first direction vents the gas through a vent in the pressure intensifier and moves the fluid through the second output port and into the first input port such that the fluid moves the bone cement out of the first output port at a second pressure that is greater than the first pressure.

3. A high pressure bone cement delivery device as recited in claim 2, wherein the first pressure is less than about 800 psi and the second pressure is greater than about 1500 psi.

4. A high pressure bone cement delivery device as recited in claim 2, wherein the bone cement has a viscosity greater than about 500 Pascal-sec (Pa-s).

5. A high pressure bone cement delivery device as recited in claim 2, wherein a pressure greater than about 800 psi is required to move the bone cement out of the first output port.

6. A high pressure bone cement delivery device as recited in claim 2, further comprising a pressurized syringe coupled to the pressure intensifier, the pressurized syringe comprising a plunger, wherein translating the plunger in the first direction translates the piston in the first direction.

7. A high pressure bone cement delivery device as recited in claim 6, wherein the pressurized syringe comprises an inner surface defining a pathway having a material disposed therein, the plunger being configured to move the material out of the pathway and into the pressure intensifier such that the material acts on the piston to move the piston in the first direction.

8. A high pressure bone cement delivery device as recited in claim 6, wherein:
the pressurized syringe is connected to the pressure intensifier by a hollow tube;
the hollow tube is coupled to an end cap; and
the pressure intensifier comprises an internal thread form that engages an external thread form of the end cap.

9. A high pressure bone cement delivery device as recited in claim 1, wherein:
axial translation of the piston in a first direction moves the fluid into the cavity such that the fluid acts on the actuator to move the actuator in the first direction; and
moving the actuator in the first direction causes the actuator to act on the bone cement to move the bone cement through the first output port.

10. A high pressure bone cement delivery device as recited in claim 1, wherein:
the pressure intensifier is connected to the delivery adapter by a hollow tube;
the hollow tube is coupled to the second output port; and
the pressure intensifier comprises an internal thread form that engages an external thread form of the hollow tube.

11. A high pressure bone cement delivery device as recited in claim 1, wherein the first and second end portions of the piston each comprise a groove having an O-ring disposed therein, the O-rings engaging an inner surface of the pressure intensifier that defines the first and second chambers to create a water tight seal.

12. A high pressure bone cement delivery device as recited in claim 1, wherein the first chamber has a diameter that is greater than that of the second chamber.

13. A high pressure bone cement delivery device as recited in claim 1, wherein the gas is air and the fluid is hydraulic fluid.

14. A high pressure bone cement delivery device as recited in claim 1, wherein the second portion is removably attached to the first portion, and detachment of the first and second portions from one another affords access to the internal cavity.

15. A high pressure bone cement delivery device as recited in claim 1, further comprising first threads provided on the first portion, and second threads provided on the second portion, the first and second threads facilitating attachment of the first and second portions to one another.

16. A high pressure bone cement delivery device as recited in claim 1, wherein the actuator includes a leading end surface and a trailing end surface, the leading end surface being at least partially convex, and the portion of the second portion received in the internal cavity includes a first surface being at least partially concave, and wherein the actuator is in the second position, the leading end surface of the actuator contacts the first surface of the portion of the second portion received in the internal cavity.

17. A high pressure bone cement delivery device comprising:
a delivery adapter comprising a first input port adjacent a first end thereof, a second output port adjacent a second end thereof, an internal cavity portion, an actuator movably disposed in the internal cavity portion, and a bone cement receiving area defined in part by the internal cavity portion and the actuator, the second output port comprising a first section having a maximum diameter that is less than a maximum diameter of the internal cavity portion, a second section having a maximum diameter that is less than half of the maximum diameter of the first portion and a tapered section that connects the first section with the second section, the actuator being moveable between a first position adjacent the first end and a second position adjacent the second end, the bone cement receiving area being larger with the actuator in the first position than with the actuator in the second position, movement of the actuator from the first position to the second position decreasing the size of the bone cement receiving area and forcing bone cement received therein to exit the internal cavity portion through the first output port, the delivery adapter having a first portion extending from the first end toward the second end, a second portion extending from the second end toward the first end, the first portion comprising a threaded outer surfaces that engages a threaded inner surface of the second portion to attach the first and second to one another, the internal cavity portion being formed in the first portion, the first output port being formed in the second portion, and a portion of the second portion being received in the internal cavity portion;
a pressure intensifier connected to the delivery adapter by a hollow tube, the pressure intensifier comprising:
a body including a first chamber containing a gas and a second chamber containing a hydraulic fluid,
a piston having a first end portion movably disposed within the first chamber and a second end portion movably disposed in the second chamber, the first end portion of the piston comprising a first end surface having a first surface area, and the second end portion of the piston comprising a second surface area, the first surface area being greater than the second surface area, the first and second end portions of the piston each comprising a groove having an O-ring disposed therein, the O-rings engaging an inner surface of the pressure intensifier that defines the first and second chambers to create a water tight seal, and
a second output port in communication with the second chamber and the input port, the second output port comprising a connector that is removably coupled to the body, the connector having a first end that includes a first pathway and a second end that includes a second pathway, the first pathway having a diameter that is less than a minimum diameter of the second chamber, the second pathway having a diameter that is less than the diameter of the first pathway;
a tube having a first end that is coupled to the second end of the connector and a second end that is coupled to the first input port; and
a pressurized syringe connected to the pressure intensifier by a hollow tube, the pressurized syringe comprising an inner surface defining a pathway having a second hydraulic fluid and a plunger disposed therein,
wherein the first chamber has a diameter that is greater than that of the second chamber,
wherein the gas has a first pressure when the gas is disposed in the first chamber, and
wherein axial translation of the plunger in a first direction moves the hydraulic fluid into the pressure intensifier such that the second hydraulic fluid moves the piston in a first direction such that the gas is vented through a vent in the pressure intensifier and the hydraulic fluid moves through the second output port and into the first input port such that the hydraulic fluid acts on the actuator such that the actuator moves the bone cement out of the first output port at a second pressure that is greater than the first pressure.

18. A high pressure bone cement delivery device as recited in claim 17, wherein the second portion is removably attached to the first portion, and detachment of the first and second portions from one another affords access to the internal cavity.

19. A high pressure bone cement delivery device as recited in claim 17, further comprising first threads provided on the first portion, and second threads provided on the second portion, the first and second threads facilitating attachment of the first and second portions to one another.

20. A high pressure bone cement delivery device as recited in claim 17, wherein the actuator includes a leading end surface and a trailing end surface, the leading end surface being at least partially convex, and the portion of the second portion received in the internal cavity includes a first surface being at least partially concave, and wherein the actuator is in the second position, the leading end surface of the actuator contacts the first surface of the portion of the second portion received in the internal cavity.

* * * * *

UNITED STATES PATENT AND TRADEMARK OFFICE
CERTIFICATE OF CORRECTION

PATENT NO. : 10,098,682 B2
APPLICATION NO. : 14/305850
DATED : October 16, 2018
INVENTOR(S) : Sasaki et al.

Page 1 of 1

It is certified that error appears in the above-identified patent and that said Letters Patent is hereby corrected as shown below:

In the Specification

In Column 5, Line 25, delete "polyaetide," and insert -- polypeptide, --, therefor.

In Column 5, Line 26, delete "polycaroplaetohe," and insert -- polycaprolactone --, therefor.

In Column 6, Line 41, delete "O-ring 37a." and insert -- O-ring 37b. --, therefor.

In Column 12, Lines 30-31, delete "recess 29 and" and insert -- recess 29a and --, therefor.

In Column 12, Line 46, delete "the facture" and insert -- the fracture --, therefor.

Signed and Sealed this
Eighth Day of October, 2019

Andrei Iancu
*Director of the United States Patent and Trademark Office*